United States Patent [19]

Adahan

[11] Patent Number: 5,419,687
[45] Date of Patent: May 30, 1995

[54] FLUID PUMP AND SUCTION PUMP ASSEMBLY INCLUDING SAME

[76] Inventor: Carmeli Adahan, Netivei Am 11, Ramot 3, Jerusalem, Israel

[21] Appl. No.: 202,954

[22] Filed: Feb. 28, 1994

[51] Int. Cl.⁶ .................................................. F04B 17/00
[52] U.S. Cl. ...................................... 417/412; 417/472
[58] Field of Search ..................... 417/413 R, 412, 472

[56] References Cited

U.S. PATENT DOCUMENTS

| | | | |
|---|---|---|---|
| 1,351,210 | 8/1920 | Heiliger | 417/412 |
| 1,793,513 | 2/1931 | Schneider | 417/472 |
| 1,992,491 | 2/1935 | Lindsay | 417/413 R |
| 2,849,152 | 8/1958 | Kaufmann | 417/412 X |
| 4,726,745 | 2/1988 | Adahan | 417/413 |
| 5,096,392 | 3/1992 | Griebel | 417/413 R |
| 5,116,206 | 5/1992 | Adahan | 417/234 |

*Primary Examiner*—Richard E. Gluck
*Attorney, Agent, or Firm*—Ladas & Parry

[57] ABSTRACT

A fluid pump includes a housing constituted of a base integrally formed with an annular wall defining a fluid reservoir and carrying an electrical pumping device, and a casing enclosing the pumping device. One side of the casing is open and is attached to the base. The opposite side of the casing is closed but includes an opening snugly receiving the annular wall of the fluid reservoir for rigidifying the housing. The pumping device includes a bellows attached at one end to the annular wall and at the opposite end to a push rod coupled by a crank to an electrical motor.

18 Claims, 3 Drawing Sheets

FLUID PUMP AND SUCTION PUMP ASSEMBLY INCLUDING SAME

FIELD AND BACKGROUND OF THE INVENTION

The present invention relates to a fluid pump which can be constructed to operate either as a suction pump or as a compressor. The invention is particularly useful in suction pump assemblies for drawing off waste fluids, for example in medical applications, and is therefore described below with respect to such application.

Many constructions have been developed for fluid pumps particularly useful in medical applications for drawing off waste fluids. Examples of such pumping devices are described in my prior U.S. Pat. Nos. 4,726,745 and 5,116,206. The fluid pump described in the first patent is based on the use of a rolling diaphragm; whereas the pump described in the second patent utilizes a piston reciprocated within a cylinder.

An object of the present invention is to provide a fluid pump which may be constructed of a few relatively simple parts and which can be produced and assembled in volume and at relatively low cost. Another object of the invention is to provide a suction pump assembly including the novel fluid pump and also a liquid collection container to be attached to the fluid pump. A further object is to provide a liquid collection container of a novel construction providing a number of important advantages.

BRIEF SUMMARY OF THE INVENTION

According to one aspect of the present invention, there is provided a fluid pump comprising: a housing having a fluid reservoir formed at one end with a fluid inlet port, and at the opposite end with a fluid outlet port; an annular wall defining the fluid reservoir between the two ports; a pumping device including an electrical motor for pumping a fluid into the fluid reservoir via a pumping opening in the annular wall; and a valve assembly within the fluid reservoir producing a positive pressure at one of the ports and a negative pressure at the other of the ports. The housing includes a cover integrally formed with the reservoir and carrying the electrical motor, and a casing enclosing the motor and pumping device. One side of the casing is open and is attached to the cover. An opposite side of the casing is closed but includes an opening snugly receiving the annular wall of the fluid reservoir for rigidifying the housing.

According to further features in the preferred embodiments of the invention described below, the pumping device includes a single bellow attached at one end to the annular wall to enclose the pumping opening therethrough leading into the fluid reservoir. The opposite end of the single bellow is coupled to a push rod which is reciprocated by the motor to pump fluid via the pumping opening into and out of the single bellow.

More particularly, in the described preferred embodiments, the single bellow is formed with side walls joined by an annular juncture. The annular juncture is of greater thickness than the side walls such as to impart to the single bellow a low yielding resistance in the axial direction, and a higher yielding resistance in the lateral direction.

A fluid pump constructed in accordance with the foregoing features requires but a few simple parts which can be produced and assembled in volume and at relatively low cost.

According to a further aspect of the invention, there is provided a liquid collection container particularly useful with the fluid pump and including an overflow shutoff valve comprising an annular shutoff section closed at one end and open at its opposite end; a mounting section for mounting the shutoff section with its closed end facing the vacuum inlet port of the container and its open end facing the interior of the container; and a yieldable juncture section integrally formed with the mounting section and the shutoff section, normally maintaining the shutoff section spaced from the vacuum inlet port, but permitting the shutoff section to close the vacuum inlet port when the liquid collected in the container reaches a predetermined level.

According to further features in the described preferred embodiment, the cover of the container is integrally formed with a pair of depending pins adjacent to the vacuum inlet port, and the mounting section of the overflow shutoff valve is formed with a pair of eyelets receiving the depending pins with a press-fit.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
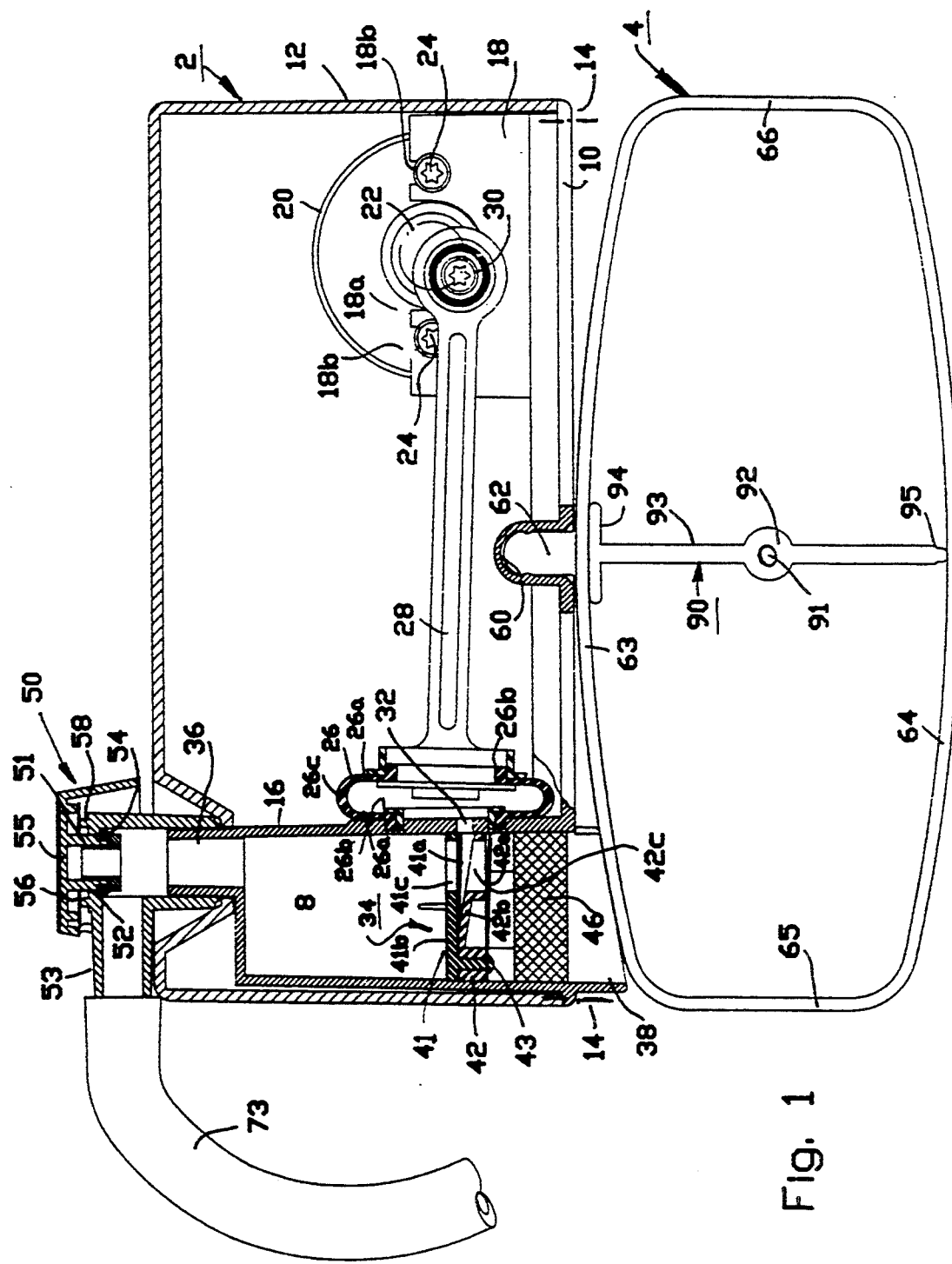
FIG. 1 is a view partly in section illustrating one form of suction pump assembly constructed in accordance with the present invention, including a fluid pump and a liquid collection container attached thereto.
Figure 2:
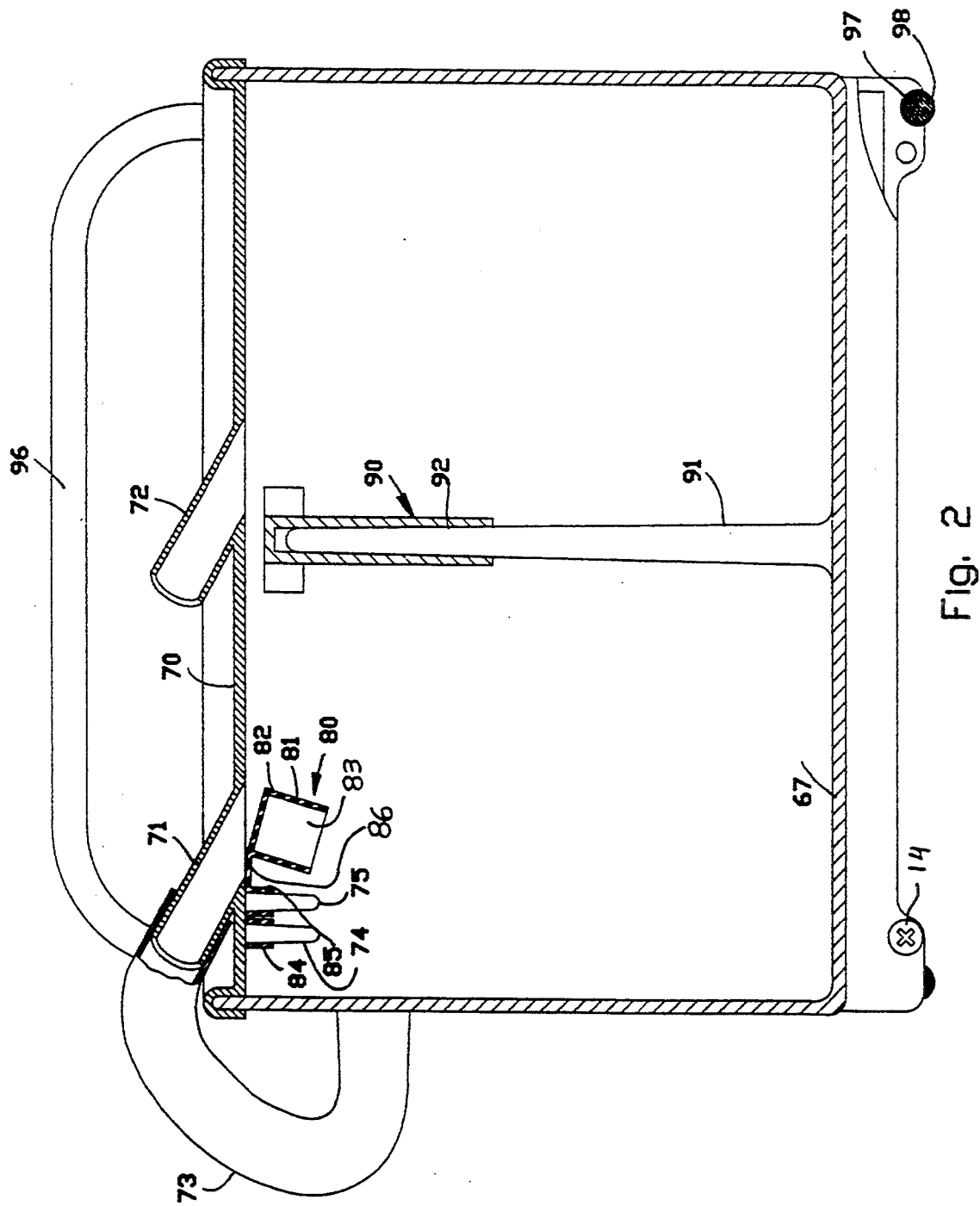
FIG. 2 is a sectional view illustrating only the liquid collection container of the assembly of FIG. 1.
Figure 3:
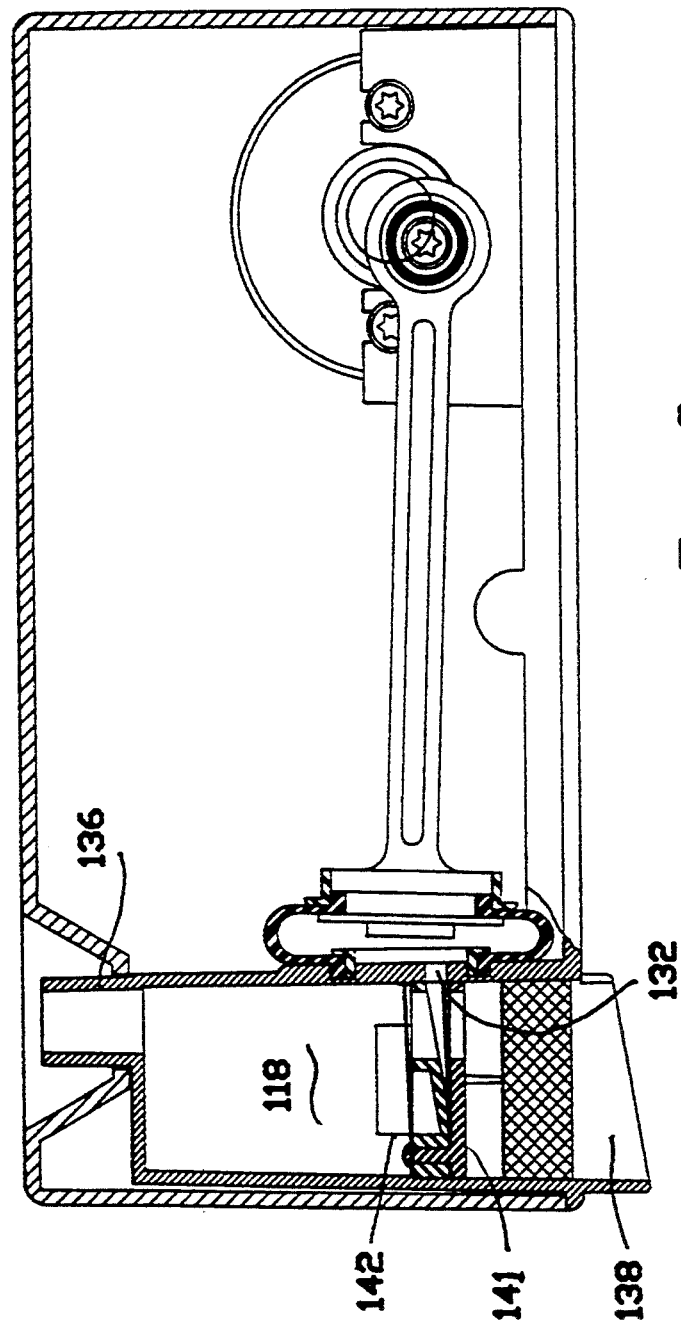
FIG. 3 is a sectional view illustrating the fluid pump of FIG. 1 but with the valve assembly changed so that the pump serves as a compressor rather than as a suction pump.

The fluid pump illustrated in the drawings may be used either as a suction pump or as a compressor by merely making a slight change in a valve assembly. FIGS. 1 and 2 illustrate the fluid pump used as a suction pump; whereas FIG. 3 illustrates the same construction with a slight modification to enable it to be used as a compressor.

The Embodiment of FIGS. 1 and 2

The suction pump illustrated in FIG. 1, therein generally designated 2, is part of suction pump assembly which includes a liquid collection container, generally designated 4, for drawing off waste fluids, e.g., in medical applications. FIG. 2 more particularly illustrates the construction of the liquid collection container 4.

The suction pump 2 comprises a cover 10 and a casing 12 attached to the cover in any suitable manner, e.g., as by fasteners shown at 14 in FIG. 2. Cover 10 is of moulded plastic material integrally formed with an annular wall 16, preferably of cylindrical configuration, defining a vacuum reservoir 8. Cover 10 is further integrally formed with a pair of spaced ledges, one of which is shown at 18 in FIG. 1, for mounting an electrical motor 20. The two ledges 18 are formed with a large semi-circular recess 18a centrally of the ledges for accommodating the eccentric 22 of motor 20, and with a pair of smaller semi-circular recesses 18b on opposite sides of the central recess 18a for receiving screws 24 which fasten motor 20 to ledge 18.

Motor 20 drives a bellows 26 via a push rod 28 fixed at one end to the bellows, and at the opposite end to eccentric crank 22 via ball bearing 30. The single bellow 26 is fixed to the inner wall 16 of the fluid reservoir 18 to enclose a pumping opening 32 formed in wall 16. It will thus be seen that reciprocation of push rod 28 by the rotation of the motor drive shaft 22 will drive bellows 16 through contraction and expansion strokes with respect to the pumping opening 32 and the vacuum reservoir 8.

Single bellow 26 is made of an elastomeric material, such as rubber. It is constituted of opposed side wall sections 26a, 26b joined by an annular juncture section 26c extending peripherally around the side wall sections. The two side wall sections 26a, 26b are relatively thin, whereas the annular juncture section 26c is of greater thickness, such as to impart to the single bellow 26 a relatively low yielding resistance in the axial direction, and a higher yielding resistance in the lateral direction.

One end of single bellow 26 is formed with a relatively thick annular bead 26d received within an annular groove formed in wall 16 of the vacuum reservoir. The opposite end of the bellow is formed with a relatively thick annular bead 26e received within an annular socket formed in the respective end of the push rod 28.

Disposed within the vacuum reservoir 8 is a valve assembly, generally designated 34. This assembly includes two one-way valves oriented to produce a negative pressure at the opposite end of the vacuum reservoir 8. In the example illustrated in FIG. 1, valve assembly 34 produces a negative pressure at end 36 of the vacuum reservoir 8, and a positive pressure at the opposite end 38. Thus, end 36 of annular wall 16 defines a negative-pressure port, whereas end 38 is open to the atmosphere. To produce this arrangement, valve assembly 34 includes one-way valve 41 on the side of the pumping opening 32 which faces the negative pressure port 36 and which permits air flow only in the direction away from the negative-pressure port; and a one-way valve 42 on the side of the pumping opening which faces end 38 and which permits air flow only in the direction towards the atmosphere.

One-way valve 41 is in the form of a resilient leaf 41a carried by a mounting member 41b formed with an opening 41c which is normally covered by the resilient leaf 41a. Mounting member 41b is of the same external configuration and dimensions as the internal configuration and dimension of annular wall 16, such that the mounting member 41a may be press-fitted into the annular wall on one side of the pumping opening 32. In the example illustrated in FIG. 1 annular wall 16 is of cylindrical configuration, and therefore mounting member 41b is of circular configuration. When mounting member 41b is press-fitted within cylindrical wall 16, resilient leaf 41a is on the pumping-opening 32 side of the mounting member, such that the leaf blocks the flow through opening 41c in the direction of the negative-pressure port 36, but permits the flow through opening 41c only in the direction towards the positive-pressure port 38.

One-way valve 42 is similarly constructed with a resilient leaf 42a and a circular mounting member 42b formed with an opening 42c covered by the resilient leaf valve 42a; however, it is press-fitted into cylindrical wall 16 on the opposite side of the pumping opening 32. Reslient leaf valve 42a is on the positive-pressure port 38 side of the mounting member 42a, so that it also permits air flow only in the direction towards the positive-pressure port.

To facilitate assembling the two one-way valves, mounting member 41b is formed with a pair of depending pins 43, and mounting member 42b is formed with a corresponding pair of holes receiving pins 43 with a press-fit. In addition, the face of mounting member 42a facing mounting member 40a is formed with a slanted surface, to define a space 44 between the two mounting members aligned with opening 32 for the air to flow through that opening.

A sound muffler member 46, also of cylindrical configuration, is press-fitted into end 38 of the cylindrical wall 16 to muffle the sounds produced by the air escaping through that port.

The negative-pressure port 36 includes a presettable device, generally designated 50, which enables presetting the vacuum produced at that port. Presettable device 50 may be of the same construction as described, for example, in my U.S. Pat. No. 5,116,206. Briefly, it comprises a cylindrical plug 51 slidably and rotatably movable within a cylindrical opening 52 formed in an elbow fitting 53 attached to the negative-pressure port 36 and passing through the casing 12 of the pump housing. The inner end of plug 51 carries a sealing ring 54 normally engageable with the inner face of elbow fitting 53. The outer end of the plug carries an enlarged knob 55 permitting the plug to be manually rotated. An arched leaf spring 56 passes through an opening in the outer end of plug 51 so as to be rotatable with the plug. The outer ends of leaf spring 56 is engageable with a plurality of discrete projections, e.g., 58 of different heights arranged in a circular array around the opening 52 in the elbow fitting 53.

The arrangement is such that the height of the projections 58 engaging the ends of the leaf spring 56 will determine the outward force applied by the leaf spring to plug 51, and therefore the degree of vacuum required to be produced within the vacuum reservoir 18 to pull the plug inwardly to unseat its seal 54. So long as the vacuum within the vacuum reservoir 18 is less than that preselected by the rotary position of plug 51, seal 54 will be firmly pressed by the leaf spring 56 against the inner surface of the housing to seal opening 52. However, whenever the vacuum exceeds the preset value, the vacuum will draw plug 51 inwardly against the force of the leaf spring 56 to unseat seal 54, and thereby to release the vacuum within the vacuum chamber 18 until the vacuum reaches the level preset by plug 51.

Cover 10 of pump 2 is further formed with a socket 60 for receiving an attachment connector 62 carried by the liquid collection container 4 to facilitate attaching that container to the pump. When the liquid collection container 4 is so attached to the pump 2, a side wall of the container engages the outer edge of end 38 of the annular wall 16, thereby further muffling the sounds produced by the air escaping from that end during the operation of the pump.

The liquid collection container 4 is formed with a pair of opposed side walls 63, 64, a pair of opposed end walls 65, 66, and a bottom wall 67. The upper end of the container is open and is closed by a cover 70. Projection 62 of the container received within socket 60 of the pump 2 projects from side wall 63, as seen in FIG. 1.

Cover 70 is also integrally formed with a vacuum inlet port 71 and with a liquid inlet port 72, as shown in FIG. 2. The negative-pressure port 36 of the vacuum reservoir 18 is connected to vacuum inlet port 71 by a tube 73 having one end received in elbow fitting 53 attached to the pump 2.

As shown in FIG. 2, the vacuum inlet port 71 of the liquid collection container 4 is formed in a cover 70 at an angle with respect to the cover; that is, the axis of the vacuum inlet port 71 is at an acute angle, preferably about 30°, to the plane of cover 70. Liquid inlet port 72 in cover 70 is also at the same acute angle with respect to the cover. The liquid inlet port 72 is adapted to receive a tube (not shown) leading to the source of the liquid to be drawn into the liquid collection container 4 by the vacuum produced at the vacuum inlet port 71.

Forming the two ports 71 and 72 at an angle as illustrated in FIG. 2, rather than perpendicularly to the cover 70, permits the ends of the tubes to which these ports are attached to assume a substantially horizontal position with less danger of forming a kink in the tube tending to obstruct the passage of air or liquids therethrough. The foregoing is thus advantageous over the conventional constructions wherein corresponding ports extend substantially perpendicularly to their respective covers and therefore are more likely to kink the tubes attached to them.

Also, fluid entering port 72 at an angle at high velocity, will hit the side wall 66 of fluid collection container 4, running down the wall without agitating the fluid already in the container. Vertical fluid entry ports cause fluid turbulance which does not permit use of the full volume of the fluid container, since the turbulant fluid causes the shutoff valve 80 to float and shut off the vacuum inlet port 71.

Cover 70 closing the upper end of the liquid collection container 4 is made of a semi-flexible material, and is integrally formed with the two ports 71, 72. Cover 70 is also formed with a pair of depending pins 74, 75 at one side of the vacuum inlet port 71 and aligned with that port. The two pins 74, 75 are adapted to receive an overflow shutoff valve 80 to block the vacuum inlet port 71 and thereby to prevent overflow into that port of the liquid collected in container 4.

The overflow shutoff valve 80 includes an annular shutoff section 81 closed at one end 82 and open at its opposite end 83, and a mounting section formed with a pair of eyelets 84, 85 adapted to receive with a press fit the pins 74, 75 of the cover 70. The above sections of valve 80 are integrally formed of a single member of elastomeric material and are connected together by a yieldable juncture section 86. The overflow valve is mounted by press-fitting the eyelets 84, 85 into the pins 74, 75, with the closed end 82 of the shutoff section 81 facing the vacuum inlet port 71, and the open end 83 of that section facing the interior of the container.

FIG. 2 illustrates the normal position of the shutoff section 81, wherein it will be seen that the closed end 82 of that section is spaced from the negative pressure port 71, thereby passing the negative pressure at that port into the interior of the container. Accordingly, when the liquid inlet port 72 is connected by a tube (not shown) leading to a liquid to be drawn away, such liquid will be drawn via inlet port 72 into container 4. Should the level of the liquid rise to the level of the shutoff section 81 of overflow valve 80, that section will float on top of the liquid and will be moved against the vacuum inlet port 71, to thereby prevent such liquid from being drawn into the pump 2 via port 71.

Container 4 further includes a spacer wall 90 engaging the inner surfaces of the two side walls 63, 64, to maintain the spacing between them and thereby to mechanically reinforce the container. The sprue 91 produced in the bottom wall 67 during the moulding process may be retained, and not removed as is the general case, and used as a projection for receiving the spacer 90.

For this purpose, spacer 90 is formed with a central tubular section 92 to be press-fitted over the sprue 91 (or other projection in the bottom wall 67), and an elongated spacer section 93 of a length equal to the width of container 4 between the two side walls 63, 64. One end of spacer section 93 terminates in a T-formation having perpendicular legs 94 to provide an extended surface area engageable with the inner surface of side wall 63. The opposite end of spacer section 93 is of reduced diameter, preferably rounded, to engage the inner surface of the opposite side wall 64, and thereby to firmly wedge the spacer wall 90 between the two side walls.

Spacer 90 thus supports the flexible cover 70 from collapsing inwardly, and also supports the opposed side wall from being drawn inwardly, when high vacuum is present within the container.

The height of spacer wall 92 is substantially less than the complete height of the container 4. In the example shown in FIG. 2, it is about one-half the height of the container, so as to provide a common volume below the spacer wall for receiving the collected liquid.

Casing 12 of the pump 2, includes a handle 96 for portability. The bottom of casing 12 is formed with a pair of semi-circular recesses 97 extending transversely across its opposite ends for the complete width of the casing. Recesses 97 receive elastomeric beads 98 of cylindrical configuration which are press-fitted into these recesses, and thereby serve as feet for supporting the pump and the liquid collection container on any suitable horizontal surface.

Manner of Use

The manner of using the suction pump assembly illustrated in FIGS. 1 and 2 will be apparent from the above description. Thus, the liquid collection container 4 is applied to the pump 2 by press-fitting projection 62 of the container into socket 60 formed in cover 10 of the pump 2. Tube 73 is then applied to elbow fitting 53 of the pump negative-pressure port 36, and to the vacuum inlet port 71 of container 4. Another tube (not shown) is applied from the liquid inlet port 72 of the container to the source of liquid to be drawn into the container during the operation of the pump.

The suction to be produced may be preset by presettable device 50, as described above.

Electrical motor 20 is then energized which drives single bellow 26, coupled to the motor via eccentric 22 and push rod 28, through expansion and contraction strokes. During the expansion strokes, air is drawn into the single bellow from the interior of the vacuum reservoir 18 via one-way valve 40 and pumping opening 32; and during contraction strokes, the air is forced out of the bellow via pumping opening 32 and one-way valve 42. Thus, a negative-pressure is produced at port 36 of the vacuum reservoir 18.

This negative pressure at port 36 is communicated via tube 73 and port 71 of the liquid collection container 4, to thereby produce a vacuum within that container. This vacuum draws into the container the liquid from the site receiving the tube (not shown) connected to the liquid inlet port 72 of the container.

If the liquid should rise to the level of the shutoff member 81 of overflow valve 80, the latter member will float to block the vacuum inlet port 71 of the container, thereby preventing the liquid from being drawn into the pump.

During this operation of the pump, muffler 46 received within the positive pressure port 38 muffles the sound generated by the air escaping through port 38. This sound is further muffled by the fact that port 38 is engaged also by side wall 63 of the liquid collection container 4.

The Embodiment of FIG. 3

FIG. 3 illustrates only the pump 2 of FIG. 1 but with the two one-way valves 141, 142 oriented to reverse the pressures produced at the two ends of the reservoir so that the reservoir, designated 118 now becomes a pressure reservoir. This can be done simply by reversing the two one-way valves press-fitted into the vacuum chamber. Thus, as shown in FIG. 3, one-way valve 141 (corresponding to valve 41 in FIG. 1) is inserted into the pressure reservoir to be located below opening 132, whereas the other one-way valve 142 is inserted to be located above the opening. In such an arrangement, the port designated 136 now becomes a positive-pressure port, whereas the end designated 138, normally negative, is connected to the atmosphere.

In all other respects, the compressor pump illustrated in FIG. 3 is constructed and operates in the same manner as described above with respect to the suction pump of FIG. 1.

While the invention has been described with respect to one preferred embodiment, it will be appreciated that this is set forth merely for purposes of example, and that many other variations, modifications and applications of the invention may be made.

I claim:

1. A fluid pump comprising:
   a housing having a fluid reservoir formed at one end with a fluid inlet port, and at the opposite end with a fluid outlet port;
   an annular wall defining said fluid reservoir between the two ports;
   a pumping device including an electrical motor for pumping a fluid into said fluid reservoir via a pumping opening in said annular wall;
   and a valve assembly within said fluid reservoir producing a positive pressure at one of said ports and a negative pressure at the other of said ports;
   characterized in that said housing includes:
   a cover integrally formed with said reservoir and carrying said electrical motor;
   and a casing enclosing said motor and pumping device;
   one side of said casing being open and attached to said cover, an opposite side of the casing being closed but including an opening snugly receiving said annular wall of the fluid reservoir for rigidifying the housing.

2. The fluid pump according to claim 1, wherein said pumping device includes a single bellow attached at one end to said annular wall to enclose said pumping opening therethrough leading into said fluid reservoir; the opposite end of said single bellow being coupled to a push rod which is reciprocated by said motor to pump fluid via said pumping opening with respect to said fluid reservoir.

3. A fluid pump comprising:
   a housing having a fluid reservoir formed at one end with a fluid inlet port, and at the opposite end with a fluid outlet port;
   an annular wall defining said fluid reservoir between the two ports;
   a pumping device including an electrical motor for pumping a fluid into said fluid reservoir via a pumping opening in said annular wall;
   and a valve assembly within said fluid reservoir producing a positive pressure at one of said ports and a negative pressure at the other of said ports;
   characterized in that said pumping device includes a single bellow attached at one end to said annular wall to enclose said pumping opening therethrough leading into said fluid reservoir; the opposite end of said single bellow being coupled to a push rod which is reciprocated by said motor to pump fluid via said pumping opening with respect to said fluid reservoir.

4. The fluid pump according to claim 3, wherein said push-rod is unguided between its attachment to said motor and its attachment to said single bellow.

5. The fluid pump according to claim 4, wherein said bellow is formed with side wall sections joined by an annular juncture section, said annular juncture section being of greater thickness than said side wall sections such as to impart to the bellow a low yielding resistance in the axial direction, and a higher yielding resistance in the lateral direction.

6. The fluid pump according to claim 4, wherein said one end of the single bellow is formed with a relatively thick annular bead received within an annular groove formed in said annular wall of the fluid reservoir, and said opposite end of the single bellow is formed with a relatively thick annular bead received within an annular socket formed in the respective end of said push rod.

7. The fluid pump according to claim 1, wherein said cover is integrally formed with a mounting for said electric motor, said electric motor mounting comprising a edge formed with a large recess for accommodating an eccentric coupled to the motor, and a pair of smaller recesses for receiving motor fastening screws.

8. The fluid pump according to claim 1, wherein said valve assembly includes a first one-way valve carried by a first mounting member press-fitted into said annular wall of the fluid reservoir on one side of said pumping opening; and a second one-way valve carried by a second mounting member press-fitted into said annular wall of the fluid reservoir on the other side of said pumping opening.

9. The fluid pump according to claim 8, wherein one of said valve mounting members is formed with a pin, and the other of said valve mounting members is formed with a hole receiving said pin with a press-fit.

10. The fluid pump according to claim 1, wherein said annular wail of the fluid reservoir includes a muffler member press-fitted into the end thereof defining said positive-pressure port.

11. The fluid pump according to claim 1, wherein the bottom of said pump housing is formed with semi-circular grooves extending transversely across its opposite ends, each of said grooves receiving a cylindrical bead of elastomeric material to define supporting feet at said opposite ends of the housing.

12. A suction pump assembly including a fluid pump according to claim 1, wherein its cover is further formed with a socket for receiving an attachment connector carried by a liquid collection container; and a liquid collection container having a connector for reception into said socket of the pump base.

13. The suction pump assembly according to claim 12, wherein said liquid collection container includes a housing closed at its upper end by a cover of resilient material; said cover being integrally formed with a a vacuum port having an axis at an acute angle with respect to the cover, and with a liquid inlet port also having an axis at an acute angle with respect to the cover.

14. The suction pump assembly according to claim 13, wherein said vacuum inlet port includes an overflow shutoff valve comprising:
   a floatable shutoff section closed at one end and open at its opposite end;
   a mounting section for mounting the shutoff section with its closed end facing the vacuum inlet port and its open end facing the interior of the container;
   and a yieldable juncture section integrally formed with said mounting section and said shutoff section, normally maintaining the shutoff section spaced from the vacuum inlet port, but permitting the shutoff section to close the vacuum inlet port when the liquid collected in the container reaches a predetermined level.

15. The suction pump assembly according to claim 14, wherein said cover of the container is integrally formed with a pair of depending pins adjacent to said vacuum inlet port, and said mounting section of the overflow shutoff valve is formed with a pair of eyelets receiving said depending pins with a press-fit.

16. The suction pump assembly according to claim 12, wherein said housing includes opposed side walls and a bottom wall formed with a projection on its inner surface, and a spacer wall received over said projection and extending completely across the width of the container in engagement with the inner surface of said opposed side walls.

17. The suction pump assembly according to claim 16, wherein one end of said spacer wall is of T-configuration to engage an enlarged surface of the respective side wall.

18. The suction pump assembly according to claim 16, wherein said liquid collection container engages said positive-pressure port to thereby muffle the air passing therethrough to the atmosphere.

* * * * *